US011134883B2

(12) United States Patent
Williams et al.

(10) Patent No.: US 11,134,883 B2
(45) Date of Patent: Oct. 5, 2021

(54) GASTRIC EMPTYING BREATH TESTS (71) Applicant: Advanced Breath Diagnostics, LLC, Brentwood, TN (US)

(72) Inventors: Catherine Elizabeth Williams, Nashville, TN (US); Shane Anthony Crabtree, Murfreesboro, TN (US)

(73) Assignee: ADVANCED BREATH DIAGNOSTICS, LLC, Brentwood, TN (US)

( * ) Notice: Subject to any disclaimer, the term of this patent is extended or adjusted under 35 U.S.C. 154(b) by 0 days.

(21) Appl. No.: 13/926,715

(22) Filed: Jun. 25, 2013

(65) Prior Publication Data
US 2014/0379267 A1 Dec. 25, 2014

(51) Int. Cl.
| | |
|---|---|
| *A61K 51/00* | (2006.01) |
| *A61M 36/14* | (2006.01) |
| *A61B 5/00* | (2006.01) |
| *A61B 5/08* | (2006.01) |
| *A61K 49/00* | (2006.01) |

(52) U.S. Cl.
CPC ............ *A61B 5/42* (2013.01); *A61B 5/082* (2013.01); *A61B 5/4238* (2013.01); *A61B 5/4255* (2013.01); *A61K 49/0004* (2013.01)

(58) Field of Classification Search
None
See application file for complete search history.

(56) References Cited

U.S. PATENT DOCUMENTS

| | | | | |
|---|---|---|---|---|
| 5,707,602 | A * | 1/1998 | Klein ............... | A61K 51/1206 424/1.17 |
| 7,785,569 | B2 | 8/2010 | Evans et al. | |
| 2008/0281166 | A1 | 11/2008 | Bush et al. | |
| 2012/0071728 | A1* | 3/2012 | Sitke ................. | A61K 51/1206 600/300 |

OTHER PUBLICATIONS

Shindo et al. (Digestion 2009, 79, 65-72).*
American Gastroenterological Association (Gastroenterol. 2004, 127, 1589-1591).*
Ritz et al. (Crit. Care Med. 2001, 29, 1744-1749).*
Urita et al. (J. Gastroenterol 2002, 37, 442-448).*
Schoeller et al. (Biomedical Mass Spectrometry 1978, 5, 29-31).*
Abell et al. (J. Nucl. Med. Technol. 2008, 36, 44-54).*
Altman et al., "Diagnostic tests 2: predictive values", BMJ, vol. 309, Jul. 9, 1994, p. 102.
Braden et al. "The [13C] Acetate Breath Test Accurately Reflects Gastric Emptying of Liquids in Both Liquid and Semisolid Test Meals", Gastroenterology, vol. 108, No. 4, Apr. 1, 1995, pp. 1048-1055.
Camilleri et al., "Clinical Guideline: Management of Gastroparesis", The American Journal of Gastroenterology, vol. 108, Jan. 2013, pp. 18-37.
Odunsi et al., "Optimizing Analysis of Stable Isotope Breath Tests to Estimate Gastric Emptying of Solids", Neurogastroenterology and Motility, vol. 21, No. 7, Jul. 2009, pp. 706-e38.
Parikh, "Batch Size Increase in Fluid Bed Granulation", APACE Pharma Inc., Westminister, Maryland, pp. 171-219.
International Patent Application No. PCT/US2014/043829, International Search Report & Written Opinion dated Sep. 12, 2014, 18 pages.
Pepe, "The Statistical Evaluation of Medical Test for Classification and Prediction", Oxford University Press, 2002, p. 16.
Szarka et al. "A Stable Isotope Breath Test with a Standard Meal for Abnormal Gastric Emptying of Solids in the Clinic and in Research", Clinical Gastroenterology and Hepatology, vol. 6, No. 6, Jun. 2008, pp. 635-643.
Solberg et al., "A Detection of Outliers in Reference Distributions: Performance of Horn's Algorithm", Clinical Chemistry, vol. 51, No. 12, 2005, pp. 2326-2332.
Tougas et al., "Assessment of Gastric Emptying Using a Low Fat Meal: Establishment of International Control Values", American Journal of Gastroenterology, vol. 95, No. 6, 2000, pp. 1456-1462.
Abell et al., "Consensus Recommendations for Gastric Emptying Scintigraphy: A Joint Report of the American Neurogastroenterology and Motility Society and the Society of Nuclear Medicine", American Journal of Gastroenterology, vol. 103, 2008, pp. 753-763.
Hellmig et al., "Gastric emptying time of fluids and solids in healthy subjects determined by 13C breath tests: influence of age, sex and body mass index," Journal of Gastroenterology and Hepatology, vol. 21, 2006, pp. 1832-1838.
Sanaka et al., "The Time of Peak 13CO2 Excretion: What does it Really Reflect in Gastric Emptying Breath Tests?," Digestive Diseases and Sciences, vol. 50, No. 4, Apr. 1, 2005, pp. 669-670.
Bharucha et al., "Comprehensive assessment of gastric emptying with a stable isotope breath test," Neurogastroenterology and Motility, 25(1), pp. e60-e69 (2013).
J S Lee, et al., "A Valid, Accurate, Office Based Non-Radioactive Test for Gastric Emptying of Solids," Gut 2000; 46:768-773.

* cited by examiner

*Primary Examiner* — Michael G. Hartley
*Assistant Examiner* — Melissa J Perreira
(74) *Attorney, Agent, or Firm* — Fredrikson & Byron, P.A.

(57) ABSTRACT

A breath test and a breath test method for diagnosing abnormal gastric emptying using a $^{13}C$ labeled breath test meal by identifying the time of maximum excretion of $^{13}CO_2$ in the breath samples. The test and test method include supplying a subject with the breath test meal, collecting a breath sample of the subject at a plurality of time points after the subject consumes the meal, generating measurements of $^{13}CO_2$ excretion from the breath samples, identifying a time $T_{max}$ at which $^{13}CO_2$ excretion is maximal, comparing $T_{max}$ to a cut-off value. The subject may be diagnosed as having delayed gastric emptying if $T_{max}$ is greater than the $T_{max}$ cut-off value.

8 Claims, 5 Drawing Sheets

GASTRIC EMPTYING BREATH TESTS

FIELD

The present invention generally relates to gastric emptying breath tests.

BACKGROUND

The digestive tract generally performs five functions when processing food. The functions include motility, secretory, digestive, absorptive, and elimination functions. Food processing begins in the oral cavity, which mechanically breaks down food by mastication, lubrication with saliva, and enzymatic processing. Food processing continues in the stomach where food is liquefied by gastric juices and enzymes secreted by the cells lining the stomach to produce chyme. The chyme next enters the small intestine where bile salts produced by the liver and digestive enzymes produced by the pancreas further process the chyme. The small intestine also absorbs components from the chyme through its walls. Components that are not absorbed by the small intestine enter the large intestine. Finally, the large intestine propels waste products into the colon, where they remain, usually for a day or two, until the feces are expelled by a bowel movement.

Sometimes, a person takes an abnormally long time to process food, or a person processes food abnormally fast. Such abnormal gastrointestinal functions are commonly caused by a disorder in the stomach. A stomach disorder can cause the stomach to empty food into the small intestine too quickly or after too long of a time. Stomach emptying disorders can be diagnosed by measuring the rate at which a meal empties from the stomach and enters the small intestine (the "gastric emptying rate"). When the rate is accelerated, the stomach prematurely dumps food into the small intestine, giving rise to abnormally fast rates of gastric emptying (rapid or accelerated gastric emptying). Conversely, when the rate is delayed, the stomach delays moving food into the small intestine, giving rise to abnormally slow rates of gastric emptying (delayed gastric emptying). Hence, measurements of gastric emptying rates have important clinical utility.

Various methods are known for quantitatively measuring gastric emptying rates.

One known method is scintigraphy, which has historically been considered the gold standard method of measuring gastric emptying rates. In a scintigraphy method, a subject ingests a meal including at least one edible food, a component of which has been radiolabeled with a gamma emitting radionuclide. A scintillation camera or gamma counter scans the stomach at different time points over an extended time period. The scans directly measure the gamma emissions arising from the radiolabeled meal remaining in the stomach.

Two metrics are commonly utilized in scintigraphy methods. These are (1) fraction of test meal emptied at a number of different time points and (2) the time it takes to empty 50% of a standard test meal from the stomach, or "$t_{1/2}$." A scintigraphic $t_{1/2}$ value for a test subject may be obtained from using the fraction emptied values and conducting a linear interpolation between the two time points at which scintigraphic fraction emptied values bracket 0.5 (50% emptied). Thus, scintigraphy methods use metrics that require taking measurements at a number of different time points.

Another method for measuring gastric emptying is breath testing. In a breath testing method, a subject ingests a meal including at least one edible food, a component that includes a $^{13}C$ label. As the subject's digestive tract processes the $^{13}C$ labeled food, a labeled digestive metabolite, $^{13}CO_2$, is produced which can be detected in the subject's breath. The $^{13}C$ label passes through the stomach, is absorbed by the small intestine and is metabolized by the liver to give rise to $^{13}CO_2$. The $^{13}CO_2$ then moves through the blood to the lungs and exits the body through the subject's breath. The amount of $^{13}CO_2$ in a breath sample may be measured. The rate of excretion of $^{13}CO_2$ in the breath signals the rate at which the stomach is emptying. A useful metric for reporting a breath test subject's rate of $^{13}CO_2$ excretion is the metric "kPCD" or cumulative kPCD. A kPCD value is a mathematical expression of a test subject's $^{13}CO_2$ excretion rate at any measurement time t relative to the dose of carbon-13 label contained in the test meal. Simply stated: kPCD=[% dose of carbon-13 label excreted (as $^{13}CO_2$) per minute×1000]. During breath testing, a test administrator collects breath samples from a subject at a number of different time points.

The kPCD or cumPCD measurements for breath samples can be used to calculate various metrics which can be used to diagnose rapid or delayed emptying. Such metrics preferably result in diagnoses that are the same as those determined based on scintigraphy. Breath test metrics that lead to diagnoses as close to those obtained by scintigraphy are generally preferred.

SUMMARY

Embodiments include breath tests and breath test methods for diagnosing abnormal gastric emptying. In some embodiments, the invention provides a breath test method for diagnosing delayed gastric emptying including supplying a subject with a breath test meal having a $^{13}C$ label, collecting a breath sample of the subject at a plurality of time points after the subject consumes the meal, generating measurements of $^{13}CO_2$ excretion from the breath samples, identifying a time $T_{max}$ at which $^{13}CO_2$ excretion is maximal using the $^{13}CO_2$ excretion measurements, comparing $T_{max}$ to a cut-off value, and identifying the subject as having delayed gastric emptying if $T_{max}$ is greater than the cut-off value.

In some embodiments, the breath test method for diagnosing delayed gastric emptying includes supplying a subject with a breath test meal having a $^{13}C$ label, collecting breath samples of the subject at a plurality of time points including a last breath sample after the subject consumes the meal, generating gastric emptying measurements from the breath samples, identifying a breath sample having a greatest gastric emptying measurement, and if the breath sample having the greatest gastric emptying measurement is the last breath sample, diagnosing the subject with delayed gastric emptying. In some embodiments, collecting breath test samples includes collecting a breath test sample at a time t which is prior to a time of collection of the last breath test sample, and if the breath sample having the greatest gastric emptying measurement is not the last breath sample, the method further includes comparing a gastric emptying measurement of a breath sample at time t to a cut-off value x. If the gastric emptying measurement of the breath sample at time t is less than x, the method may include diagnosing the subject as having delayed gastric emptying.

In some embodiments, the time t is between 90 and 150 minutes, such as at 120 minutes. In some embodiments, x is less than a lower limit of a normal 95% confidence interval at time t, such as between about 10% and about 50% less than a lower limit of a calculated normal 95% reference range at time t.

Other embodiments include a method for developing a breath test including performing gastric emptying breath tests on a series of normal subjects to obtain $^{13}CO_2$ excretion measurements at a series of time points, identifying a time $T_{max}$ at which gastric emptying as measured by $^{13}CO_2$ excretion is maximal for each normal subject, and calculating a 95% reference range for $T_{max}$ using the identified $T_{max}$ for the normal subjects. The breath test may be designed such that when a test subject takes the breath test, the subject would be diagnosed as having delayed gastric emptying if the test subject has a $T_{max}$ which is above the upper limit of the 95% reference range. The method may further include identifying a time t and a breath test measurement x, wherein the breath test is designed such that when a test subject takes the breath test, the subject would be diagnosed as having delayed gastric emptying if the test subject had a breath test measurement less than x at time t. For example, the method may further include performing gastric emptying breath tests on a series of abnormal subjects having delayed gastric emptying to obtain breath test measurements at said series of time points, wherein identifying a time t comprises identifying a time at which a difference between an average of the breath test measurements for the normal subjects and an average breath test measurements for the abnormal subjects is maximal. Identifying a breath test measurement x may include identifying a 95% reference range for the breath test measurements for the normal subjects at time t and selecting x as a value at or below a lower end of the 95% reference range.

The method of developing a breath test may further include selecting a time point from the series of time points as a last time point of the breath test, wherein the last time point is after the 95% reference range. In some embodiments, the average breath test measurements of the subjects having delayed gastric emptying may rise until the last time point. In some embodiments, the last time point is four hours. The breath test may be designed such that when a test subject takes the breath test, the subject would be diagnosed as having rapid gastric emptying if the test subject had a $T_{max}$ which is before the 95% confidence interval.

In some embodiments, the breath test method for diagnosing rapid gastric emptying includes supplying a subject with a breath test meal having a $^{13}C$ label, collecting breath samples of the subject at a plurality of time points after the subject consumes the breath test meal, generating $^{13}CO_2$ excretion measurements from the breath samples, identifying a time $T_{max}$ at which $^{13}CO_2$ excretion is maximal using the $^{13}CO_2$ excretion measurements, comparing $T_{max}$ to a cut-off value, and identifying the subject as normal or as having rapid gastric emptying.

In each of the embodiments described above, identifying a time $T_{max}$ may include identifying a breath sample having the greatest gastric emptying measurement, wherein $T_{max}$ is the time point at which the breath sample having the greatest gastric emptying measurement was collected. Identifying a time $T_{max}$ may include applying a mathematical equation to the gastric emptying measurements to obtain a curve of $^{13}CO_2$ excretion over time including extrapolated values, wherein $T_{max}$ comprises a time corresponding to a point on the curve at which $^{13}CO_2$ excretion is greatest.

In each of the embodiments described above, the plurality of time points may include a last time point and the $T_{max}$ cut-off value may be the last time point. This last time point may be four hours. The breath test meal may have a $^{13}C$ label in a dose of between about 20 mg to about 80 mg. The breath test meal may include a $^{13}C$-Spirulina platensis label. The breath test meal may have a caloric content of between about 200 and about 400 kCal.

BRIEF DESCRIPTION OF THE DRAWINGS

The following drawings are illustrative and therefore do not limit the scope of the invention. The drawings are not to scale (unless so stated) and are intended for use in conjunction with the explanations in the following detailed description.

DETAILED DESCRIPTION

For the purpose of promoting an understanding of the principles of the invention, various embodiments will now be described. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

Various embodiments include breath test methods that can detect, diagnose and monitor delayed gastric emptying or rapid gastric emptying by obtaining breath sample(s) over the course of the breath test evaluation period and identifying the time at which maximum $^{13}CO_2$ excretion occurs. This time point, which may be referred to as the $T_{max}$, may be used alone as a single diagnostic value, or may be used in combination with other breath test values and/or scintigraphic values to diagnose delayed or rapid gastric emptying.

The value of $T_{max}$ for an individual patient may be determined using the results of a gastric emptying breath test. $T_{max}$ is the time point at which $^{13}CO_2$ excretion reaches a maximum during the gastric emptying breath test evaluation period. In some individuals, $^{13}CO_2$ excretion increases during the early portion of the test, then reaches a maximum, and then declines during the later portion of the test. In other individuals, particularly individuals with delayed gastric emptying, $^{13}CO_2$ excretion increases throughout the duration of the test. In such individuals, $^{13}CO_2$ excretion may not truly reach a maximum until a time point that occurs after completion of the test, and therefore it is not possible to identify the time at which maximum $^{13}CO_2$ excretion actually occurs. The time point at which the test is completed, such as at four hours, may therefore be used as the time at which $T_{max}$ occurs in such cases. Though the $T_{max}$ in such cases does not represent actual time at which $^{13}CO_2$ excretion reached a maximum level, the Applicant has discovered that it can nevertheless be used to diagnose gastroparesis.

Figure 1:
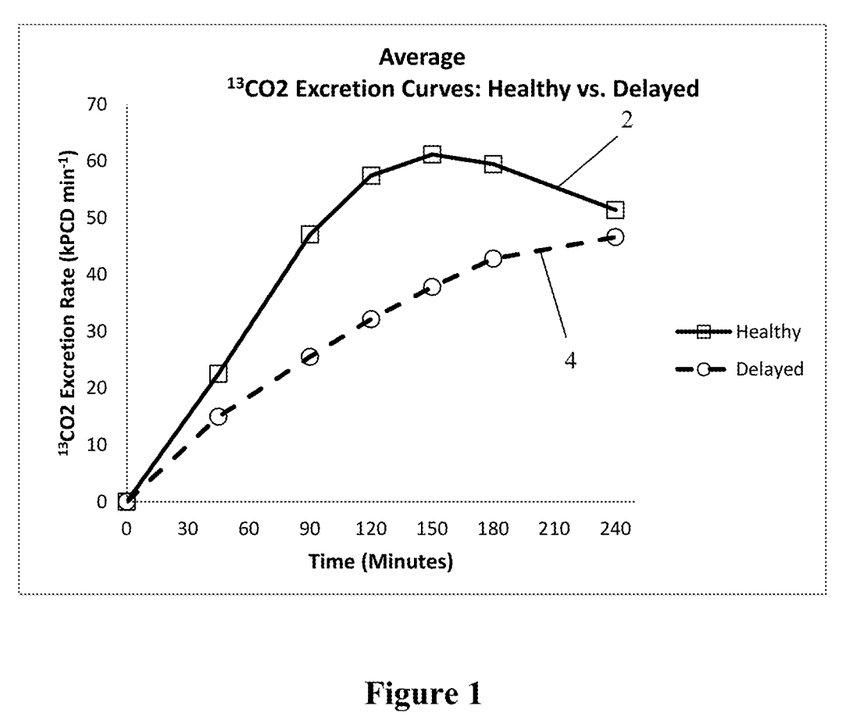
FIG. 1 is a graph of average $^{13}CO_2$ excretion profiles for a group of normal subjects and a group of subjects with delayed gastric emptying.

To better illustrate the concepts, an example of breath tests results for two different groups of individuals are shown in FIG. 1, as described further in the Examples. In FIG. 1 the top (arched) curve, line 2, reflects the mean of the kPCD values obtained at each measurement time from 60 healthy subjects, used to establish a breath test gastric emptying reference range (the "Normal Range"). The bottom curve, line 4, is the mean of the kPCD values obtained from 57 test subjects who were determined to have delayed gastric emptying (gastroparesis) by the gold standard method of gastric scintigraphy. All 117 test subjects were given the exact same breath test meal with the exact same dose of carbon-13 label. All subjects were evaluated over a 4 hour (240 minute) time period. On average, $^{13}CO_2$ excretion peaked at about 150 minutes for healthy subjects with normal rates of gastric emptying and then declined during the remaining evaluation period. However, the average $^{13}CO_2$ excretion did not reach a peak prior to 240 minutes for subjects with delayed gastric emptying. Because of this separation, subjects with normal rates of gastric emptying can be clearly differentiated from those with delayed emptying using $T_{max}$.

Figure 2:
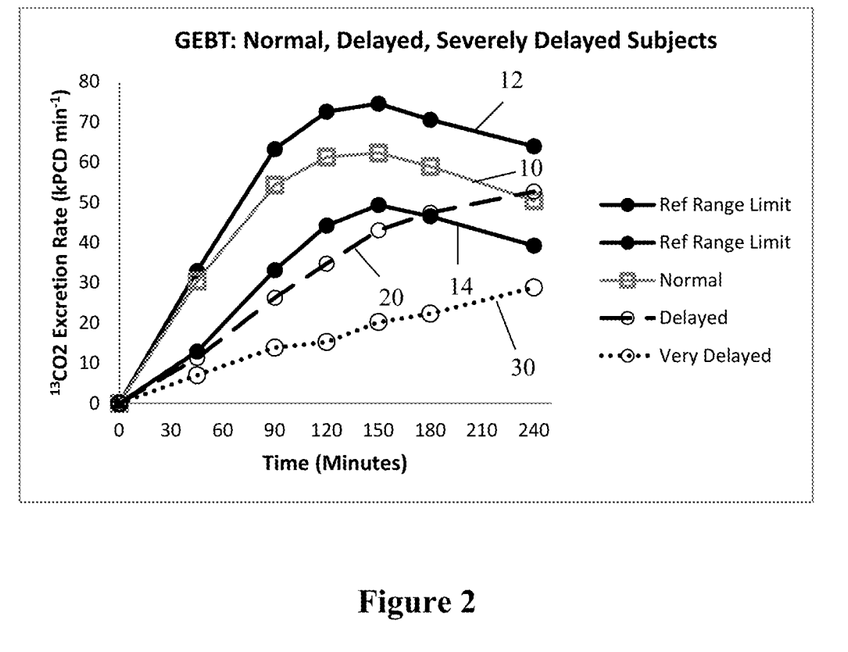
FIG. 2 is a graph of $^{13}CO_2$ excretion profiles for a normal subject, a subject with delayed gastric emptying, and a subject with very delayed gastric emptying.

FIG. 2 is a more specific example of the concept using individual test subjects. The $^{13}CO_2$ excretion curve (kPCD vs. time) of a normal individual is shown in line 10, and the upper and lower limits of the normal reference range established from the 60 healthy subjects referenced above are shown by lines 12 and 14 respectively as described in Example 1, below. The $^{13}CO_2$ excretion curve of the normal subject (line 10) rises until about 120 or 150 minutes, and then begins to decline. In contrast, lines 20 and 30 represent the excretion curves of two delayed subjects. Line 20 is a moderately delayed subject and line 30 is a severely delayed subject. Both subjects' kPCD values continuously rise throughout the evaluation period. By default, their peak excretion occurs at the end of the evaluation period, 240 minutes.

With regard to FIG. 2, it should further be observed that the kPCD results of the normal subject (line 10) fall at later times in the test period and continue to reside in the normal reference range throughout the test while the kPCD test results of the two delayed subjects (lines 20 and 30) are continuing to rise at later time points. As in this example of a subject having moderately delayed gastric emptying shown in line 20, it is typical of many patients having moderately delayed gastric emptying for the kPCD values at later time points to coincidentally rise into or through the normal reference range. For example, the normal (line 10) and the moderately delayed (line 20) subjects' excretion curves intersect at around 240 minutes. The moderately delayed subject has a 240 minute kPCD value that clearly resides in the normal reference range for that time point. However, this subject has delayed gastric emptying at earlier breath test time points and at every time point by scintigraphy and therefore has delayed emptying despite the normal kPCD value at 240 minutes.

Because $^{13}CO_2$ excretion curves (plots of kPCD vs. time) rise in normal individuals until reaching a maximum (at approximately 150 minutes on average) and then start to decline again (between 150 and 240 minutes), and the $^{13}CO_2$ excretion curves of individuals with delayed gastric emptying continuously rise and often cross through the normal reference range at later time points, there is a decrease in diagnostic sensitivity (for diagnosing gastroparesis) by kPCD metric alone when measured at 180 and 240 minutes. This decrease in diagnostic sensitivity can be observed by referring to the excretion curve of the individual with moderately delayed gastric emptying (line 20) in FIG. 2. This subject's excretion curve 20 is still rising at 180 and 240 minutes. However, at 240 minutes, this individual's kPCD value resides within the limits of the normal reference range. Without reference to test values at earlier time points or this patient's independent scintigraphic test results (which classified the subject as having delayed gastric emptying) one would classify this individual as "normal" at this measurement time. However, because this individual is known to be delayed at 240 minutes by scintigraphy, the individual's diagnostic classification by breath test (kPCD value) is wrong at this time point, giving a false normal (negative) result by breath test. In general, this crossover phenomenon results in false negative diagnoses by breath test at later time points, especially at 240 minutes as compared to classification by the gold standard method of gastric scintigraphy. Hence, the 180 and 240 minute time points are less diagnostically sensitive or useful when using only the kPCD metric while conducting breath testing. However, kPCD values at all time points are valuable for obtaining $BT\_t_{1/2}$ values, determining the time at which maximum $^{13}CO_2$ excretion occurs ($T_{max}$) and determining diagnosis by $T_{max}$. A similar crossover phenomenon may be expected to occur in patients with rapid emptying, and $T_{max}$ can also address this problem to accurately diagnose rapid emptying. In individuals with rapid emptying, kPCD profiles rise rapidly, with measurements at early time points falling above the normal reference range limit and $T_{max}$ occurring early. After reaching $T_{max}$, kPCD values may then fall into the normal range at later time points. As with delayed gastric emptying, $T_{max}$ may therefore be used to distinguish normal and abnormal individuals with rapid emptying without being confounded by some normal kPCD values.

The calculation of $T_{max}$ generally includes obtaining breath sample(s) at multiple time points after a subject ingests a test meal. One exemplary method of using a test meal with unique physiologic $^{13}CO_2$ excretion attributes in combination with identification of $T_{max}$ will now be described. When a clinician orders a breath test including identification of $T_{max}$, instructions are provided to the subject. These instructions may preferably include fasting, which may be done by the subject using any acceptable fasting protocol for a period of time before the test is administered. Before the breath test method is performed, a test administrator collects baseline breath samples from the subject. The subject then ingests a test meal that includes a $^{13}C$ label incorporated into the meal. In some cases, the breath test meal has a caloric content of between about 200 and about 400 kCal, such as preferably between about 200 and about 400 kCal in some embodiments. The caloric content and other features of the test meal may be selected such that $T_{max}$ can be used to differentiate normal from gastroparetic patients using a test of a desired duration, such as four hours. The test administrator collects a fasting, pre-meal (baseline) breath sample. The subject consumes the meal in a single setting, for example within a specific time frame. The test administrator then collects additional breath samples from the subject at specific time points after the subject ingests the meal. The test administrator generates a gastric emptying breath test measurement such as kPCD from each of the breath samples and uses the measurements to provide a $T_{max}$ test result. The gastric emptying measurements, expressed in kPCD metric, may also optionally be used to generate other results such as $BT\_t_{1/2}$.

The test meal includes a $^{13}C$ label that is incorporated into the meal. In certain cases, a $^{13}C$ label is incorporated into biomass, which is then incorporated into the test meal. For example, in specific cases, the test meal includes a $^{13}C$ label incorporated into *Spirulina platensis*. *Spirulina platensis* labeled with $^{13}C$ can be obtained by growing the algal cells in a $^{13}$C-enriched environment as is disclosed in commonly assigned U.S. Pat. No. 6,872,516, the disclosure of which is incorporated herein by reference in its entirety.

The test meal includes a $^{13}$C label at a dose that provides an excellent signal for $^{13}$CO$_2$ breath testing. In some cases, the dose is between about 20 mg and about 80 mg of $^{13}$C label or perhaps between about 40 mg and about 50 mg, such as 43 mg of $^{13}$C. In certain cases, the subject ingests $^{13}$C-*Spirulina platensis* at a dose of approximately 100 mg, which contains approximately 43 mg of $^{13}$C.

The $^{13}$C-*Spirulina platensis* may be incorporated into an edible food component that forms part of the test meal. The test meal may include any number of edible food components that can be ingested at a single setting. A single setting can be a designated time period, perhaps a period of less than 30 minutes, 20 minutes, or even 10 minutes. In many cases, the test meal can include a main food component as well as any side components and/or liquid components. In certain cases, the test meal includes food components derived from standardized, freeze-dried or lyophilized food components, such as those described in U.S. patent application Ser. No. 10/435,092, the entire contents of which are incorporated herein by reference.

In some particular embodiments, the test meal includes reconstituted lyophilized whole eggs and $^{13}$C-*Spirulina platensis* as a main food component. The $^{13}$C-*Spirulina platensis* in this embodiment is present in an amount of 100 mg (which contains approximately 43 mg of $^{13}$C). The test meal can also include bread or crackers as a side component and/or milk or water as a liquid component.

The test administrator directs the subject to deposit a breath sample into a container, such as by blowing through a straw into the bottom of a container such as a glass tube to displace contained air and capture a clean breath sample. The test administrator caps the container such as the tube. Alternatively, the subject may blow into a breath bag container, for example constructed of mylar-type material and having a valve mechanism that operates in a manner that retains the sample in the bag after depositing the breath. The $^{13}$CO$_2$ content measurement of the breath in the container is then measured, such as by an operator inserting the container into an instrument for analysis by Gas Isotope Ratio Mass Spectrometry (GIRMS), such as a mass spectrometer, infrared spectrometer or any other known instrument for measuring of $^{13}$CO$_2$/$^{12}$CO$_2$ ratios in breath, and directing the instrument to perform the measurement.

The $T_{max}$ value may be used alone or in combination with other breath test measurements or calculations to diagnose rapid or delayed gastric emptying. For example, $T_{max}$ may be used in combination with breath test results which may be expressed as kPCD and CumPCD. The PCD metric is the Percent Dose (abbreviated PCD) of $^{13}$C excreted at time t (in this case, at the single time point) after consumption of the test meal. To provide a more convenient scale, PCD is multiplied by 1000 to produce kPCD at time t. The kPCD value can be calculated as follows:

$$kPCD_t = \left[\frac{DOB * CO_2PR * R_s * 13}{10 * dose}\right] * 1000$$

where:

DOB=The measured difference in the $^{13}$CO$_2$/$^{12}$CO$_2$ ratio between the single time point measurement and the baseline measurement.

CO$_2$PR=CO$_2$ production rate (mmol CO$_2$/min) calculated using the Schofield equations. The Schofield equations are a set of equations which are fitted to people depending on their age, gender, height, and weight to estimate the basal metabolic rate (BMR), which is intimately related to $^{13}$CO$_2$ production rate. The equations are known in the art and allow the calculation of a specific CO$_2$ production rate for the individual being tested.

$R_s$=0.0112372, the ratio [$^{13}$CO$_2$/$^{12}$CO$_2$] in an international reference standard (Pee Dee Belemnite).

13=The atomic weight of $^{13}$C.

10=A constant factor for converting units.

Dose=The weight (mg) of $^{13}$C in the dose of $^{13}$C-*Spirulina platensis* administered to the subject in the test meal. For example, since $^{13}$C-*Spirulina platensis* is approximately 43% by weight $^{13}$C, a dose of 100 mg corresponds to approximately 43 mg of 130.

The $T_{max}$ value may be expressed in units of time, such as hours, minutes, and/or seconds. The $T_{max}$ result may be calculated from the breath test measurement in a variety of ways. In some embodiments, the breath test results may be applied to a mathematical program which calculates the excretion profile by interpolating values between the breath test measurements, such as by using a 5$^{th}$ order polynomial equation. The time at which $T_{max}$ occurs may then be identified by the program based on the generated excretion profile. The generated excretion profile may be provided to a clinician, such as in a graphical form like those of FIGS. 2 and 3, and the clinician may visually identify $T_{max}$.

Alternatively, in some embodiments, an individual's $T_{max}$ value may be determined by simply plotting the individual's kPCD test values versus time and identifying the breath sample time point at which the highest kPCD values occurs on the plot. Alternatively, the breath sample time point at which the highest kPCD value occurs may be determined from the numerical value of the results without using a graphical plot. If the breath test measurements (kPCD values) rise throughout the test period (no peak in the excretion curve is observed), then the last measurement time in the evaluation period, (240 minutes, for example), may be used as the time at which $T_{max}$ occurs even though maximum $^{13}$CO$_2$ excretion may actually occur much later in very delayed patients. In this way, $T_{max}$ can be determined and used for diagnosis without the need to mathematically identify $T_{max}$ with curve fitting models. As will be demonstrated, the graphical approach (or alternatively the numerical approach) is as diagnostically accurate as the curve fitting approach for establishing diagnosis by $T_{max}$. Such methods are particularly useful in embodiments using a test meal in which the normal reference range for $T_{max}$ falls before the time at which the last breath sample is collected during the test evaluation period, and the $T_{max}$ for individuals with delayed emptying occurs after the time of the last breath sample. An example of such an embodiment is a four hour gastric emptying breath test using a test meal including 43 mg $^{13}$C incorporated into *Spirulina platensis*.

In some embodiments, a $T_{max}$ may be considered normal if it falls within a normal reference range. For example, for a 4 hour breath test, the $T_{max}$ may be normal if it is less than 4 hours (that is, if it occurs before the end of the test.)

In certain cases, the $T_{max}$ can be considered normal if it is less than an upper cut-off point value and greater than a lower cut-off point value. A $T_{max}$ greater than the upper cut-off value is abnormal and indicates the presence of delayed emptying, and a $T_{max}$ less than the lower cut-off value is also abnormal and represents rapid emptying.

The cut-off values for $T_{max}$ for a particular gastric emptying test can be determined statistically using gastric emptying data from a group of normal subjects. For instance, a cohort of normal, healthy subjects can be administered a specific standardized test meal containing a $^{13}C$ label for breath testing. Each healthy subject in the cohort is tested by collecting and conducting breath test measurements at multiple time points. The $T_{max}$ may be determined for each individual, such as by using a mathematical program as described above. The $T_{max}$ results can then be arrayed. From these arrays, an upper and/or lower cut-off point can be selected. For example, a simple way to identify a cut-off point is to array the $T_{max}$ results for all subjects from high to low. The values residing at the upper and/or lower $95^{th}$ percentile of the array of values can then be used as cut-off points. Or, for example, the mean of the test values plus or minus 1.96 standard deviations can serve as cut-off points.

In some embodiments, the upper and lower cut-off points can be identified as the 0.025 fractile (2.5%) bound of the central 0.95 (95%) reference interval of $T_{max}$ values obtained from healthy subjects. The central 95% reference interval may be calculated using commercially available validated statistical programs such as RefVal and MedCalc. Factors such as the within-subject natural biologic variation of gastric emptying can also be measured and considered when determining the cut-off point between normal and delayed gastric emptying or between normal and rapid emptying. In some embodiments, the 95% level of diagnostic efficiency may be used for determining the cut-off points, while in other embodiments, the diagnostic efficiency level chosen could be set lower at the 90%, 85% or 80% level, for example. In some embodiments, the $T_{max}$ value can be used to identify a test result as normal, delayed, or borderline delayed or alternatively as normal, accelerated, or borderline accelerated. Methods for identifying the cut off points for such zones are described in U.S. Pat. Pub. No. 2008-0281166, the disclosure of which is hereby incorporated by reference.

In some embodiments, a patient with a $T_{max}$ occurring prior to the $T_{max}$ cut off point that demarcates normal from delayed rates of emptying, can be identified and be correctly diagnosed as actually having delayed gastric emptying. The applicant has discovered that in certain unusual circumstances, this can occur in individuals with severely delayed gastric emptying and therefore the diagnosis of delayed gastric emptying may be more accurate if the test properly handles such unusual individuals.

Figure 3:
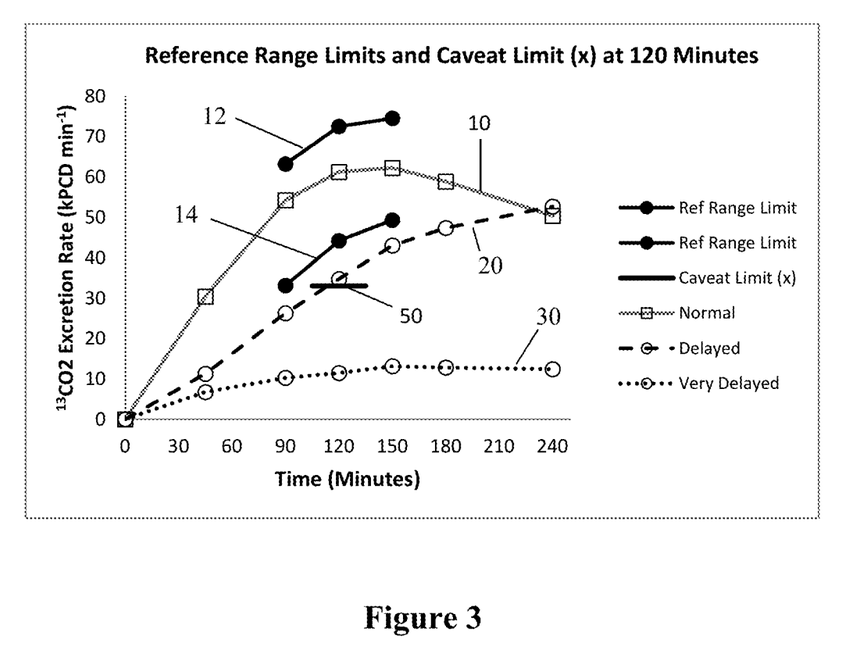
FIG. 3 is a graph of $^{13}CO_2$ excretion profiles for a subject with delayed gastric emptying and a subject with severely delayed gastric emptying.

An example of such an unusual patient is demonstrated with reference to FIG. 3. In FIG. 3, the $^{13}CO_2$ excretion curves (kPCD metric) of two delayed patients (lines 20 and 40) are superimposed on a graph of the normal kPCD reference range limits (lines 12 and 14). The moderately delayed subject, line 20, displays the typical excretion curve of almost all delayed subjects. That is, the kPCD values rise throughout the 4 hour evaluation period and exhibits maximum $^{13}CO_2$ excretion at the final 240 minute time point. However, unlike the moderately delayed subject, the excretion curve of the severely delayed subject, line 40, rises very slowly, remaining very low, and appears to be nearly horizontal. It is very unusual, but this severely delayed subject appears to show a $T_{max}$ at approximately 150 minutes, which is before the 240 minute $T_{max}$ cut-off value for this test, and therefore within the normal range for this test when using the $T_{max}$ metric. However, a normal diagnosis for this severely delayed individual would be inaccurate. Therefore, in these rare patients, in order to diagnose delayed gastric emptying, the diagnostic criteria may also include a caveat to address individuals of this type. In this example, the caveat is indicated by line 50 making the cut off point at 120 minutes to identify unusual individuals with an early $T_{max}$ but who have frank delayed gastric emptying. In this example, a diagnosis of delayed gastric emptying is made if kPCD is less than 33 at 120 minutes, even if $T_{max}$ is normal.

Because $T_{max}$ occurs late, after the normal reference range, in nearly all individuals with delayed gastric emptying, and a normal $T_{max}$ only occurs in a very small subset of individuals having severely delayed emptying, a diagnostic rule to capture these individuals is not difficult to devise. For example, a simple kPCD cut-off point at a single time point may be used which would identify all such individuals with severely delayed gastric emptying. For example, a diagnosis of delayed gastric emptying may be made if (1) the $T_{max}$ occurs on or after a specified cut-off time or (2) $T_{max}$ occurs before the specified cut-off point and the $^{13}CO_2$ excretion rate (kPCD) at a time t is less than a value x.

The values for t and x will depend on the particular test method (e.g., size of the meal, amount of $^{13}C$ included in test meal) and the limits of the established reference range. However, the time t may be selected to fall at a time or within a time window at which the maximum difference in $^{13}CO_2$ excretion occurs between normal and delayed individuals. In a 43 g $^{13}C$ test meal, this time window is between 90 minutes and 150 minutes (as demonstrated in FIG. 1), and t may be selected for any time in that window. The value of x may be selected based upon the normal 95% reference range (the lower 2.5% cut-off point) at time t. For example, x may be the lower cut-off point at time t based on a 95% reference range, or x may be less than the lower cut-off point at time t in order to avoid false negative diagnoses, given that the unusually early $T_{max}$ (with a very low kPCD value at time x) only occurs in individuals having severely delayed gastric emptying. For example, x may be the lower cut-off value. For example, x may be set at the lower cut-off value based on a 95% reference range minus about 10% and about 50% of the lower cut-off value, such as minus about 10%, or minus about 20%, or minus about 30% of the lower cut-off value. In some embodiments, the value of x for a particular t may be determined interactively by comparing diagnosis using proposed values of x to scintigraphic diagnosis to identify the value of x which resulted in the best diagnostic performance statistics.

If the $T_{max}$ result is greater than the higher end cut-off point of the normal reference range, or if the $^{13}CO_2$ excretion (kPCD) is less than x at time t, a clinician diagnoses the subject as having delayed gastric emptying. Alternatively, if $T_{max}$ is less than a lower end cut-off point for the normal reference range, a clinician diagnoses the subject as having accelerated gastric emptying. The clinician can then investigate the cause of the disorder and select an intervention program, for example for gastroparetic patients, that may include actions such as dietary changes, weight loss and/or pharmacologic intervention. For example, the clinician may prescribe for the patient a treatment plan which the patient may then implement. Examples of dietary changes include consuming meals with lower fat content and lower residue, and smaller and more frequent meals. Examples of pharmaceutical agents which may be prescribed for the treatment of gastroparesis include prokinetic agents to improve gastric emptying such as dopamine D2-receptor antagonists such as metoclopramide, type II dopamine antagonists such as domperidone, or other agents such as erythomycin lactobionate. Some subjects with severely delayed gastric emptying may suffer nutritional deficiency and therefore the clinician may prescribe intravenous feeding intervention which may be administered to the patient. Symptomatic treatment may also be prescribed and may be implemented by the patient, including antiemetic agents such as phenothiazines such as prochlorperazine and thiethylperazine or antihistamine agents such as promethazine.

After intervention, a separate follow-up breath test may be conducted and the pre and post intervention $T_{max}$ values and/or $^{13}CO_2$ excretion values at time t can be obtained. A clinician can then compare the post-treatment result with the original result, to determine whether the disorder is improving. In such cases, the $T_{max}$ value and kPCD value at time t is first used as a diagnostic health test and then is later used to monitor treatment results.

When using a unique test meal containing 27 grams of powdered egg and 100 mg $^{13}C$-*Spirulina* (43% by weight $^{13}C$) the maximum $^{13}CO_2$ excretion rate in normal subjects rarely exceeds 209 minutes (<2.5% chance) AND gastroparetic subjects rarely reach a maximum excretion rate before 240 minutes. Therefore $T_{max}$ clearly discriminates between normal and delayed subjects. The excellent utility of $T_{max}$ as a breath test diagnostic metric can be confirmed by evaluating its diagnostic precision. For example, the diagnostic precision of $T_{max}$ (used individually or in combination with a kPCD cutoff value x at time t) can be confirmed by comparing diagnosis by $T_{max}$ to diagnosis obtained by the gold standard scintigraphy method. (Diagnostic precision is then expressed using standard equations for calculating sensitivity, specificity, concordance, NPV and PPV). The diagnostic precision of $T_{max}$ can be determined against multiple scintigraphic metrics used for diagnosis, such as fraction of meal emptied at time t, or scintigraphic $t_{1/2}$. $T_{max}$ and $BT\_t_{1/2}$ (a metric calculated from kPCD results using Multiple Linear Regression (MLR) equations that generate a value equivalent to a Scintigraphic $t_{1/2}$) values may be co-reported with kPCD test results obtained at 90, 120 and 150 minutes. All test results across the 3 metrics are diagnostically useful and may be used individually or in combination by a clinician. A breath test report may also include a graphical display of the subject's breath test results ($^{13}CO_2$ excretion curve) across all measured time points out to 4 hours, for example. The subject's $^{13}CO_2$ excretion curve (kPCD metric) may be displayed relative to the normal reference range established for the measured time points, such as the 90, 120 and 150 minute time points where discrimination between normal and delayed subjects is best. The breath test results and the graphical display of $^{13}CO_2$ excretion curve may provide clinicians with a comprehensive gastric emptying profile from which a diagnosis may be made. Diagnosis of gastroparesis may be made based on $T_{max}$ alone or in combination with a cutoff value x at time t, and/or in combination with one or more other breath test metrics, such as $BT\_t_{1/2}$ and kPCD test results, optionally including a graphical display.

Figure 4:
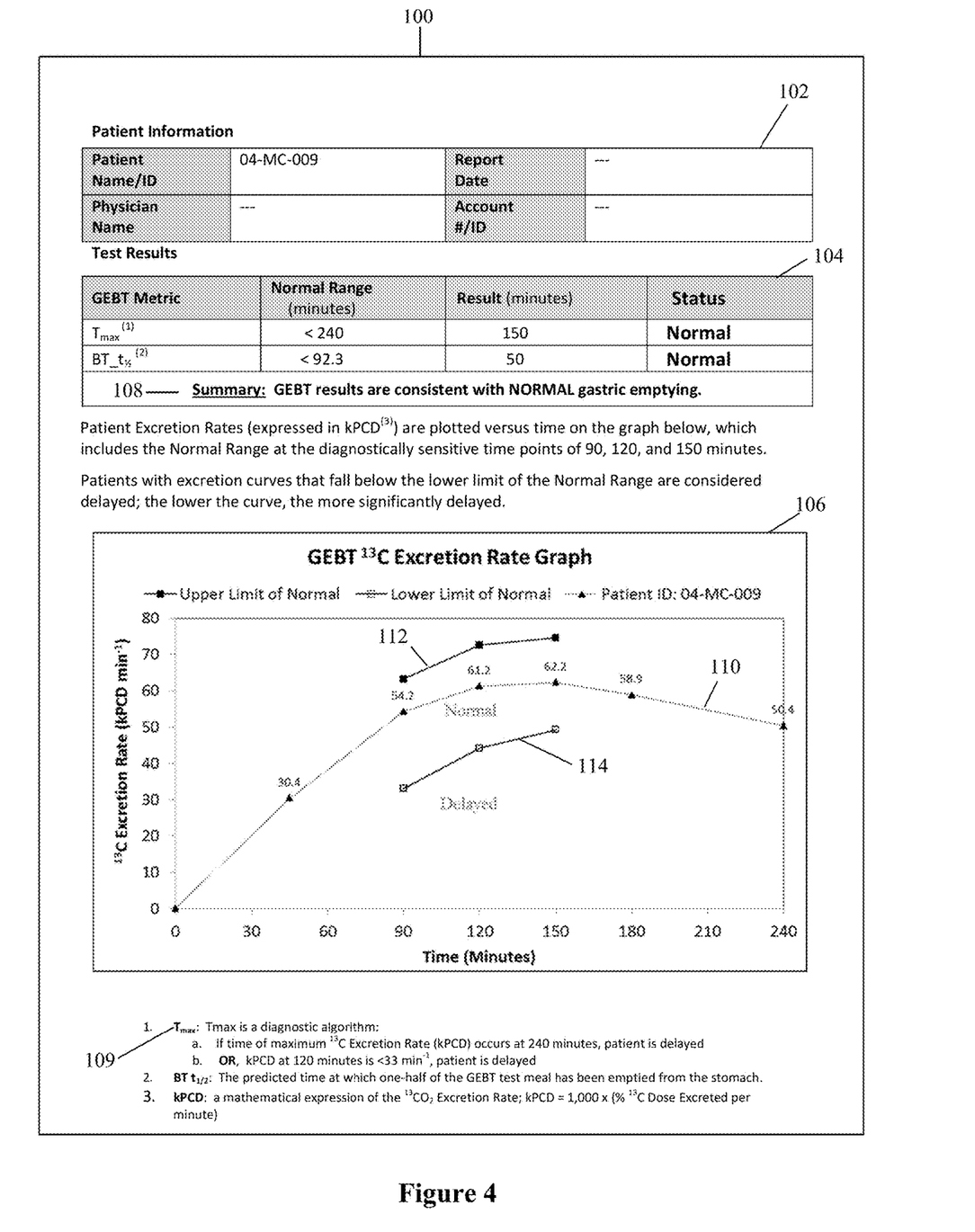
FIG. 4 is a report including a graph of a $^{13}CO_2$ excretion profile for a normal subject.
Figure 5:
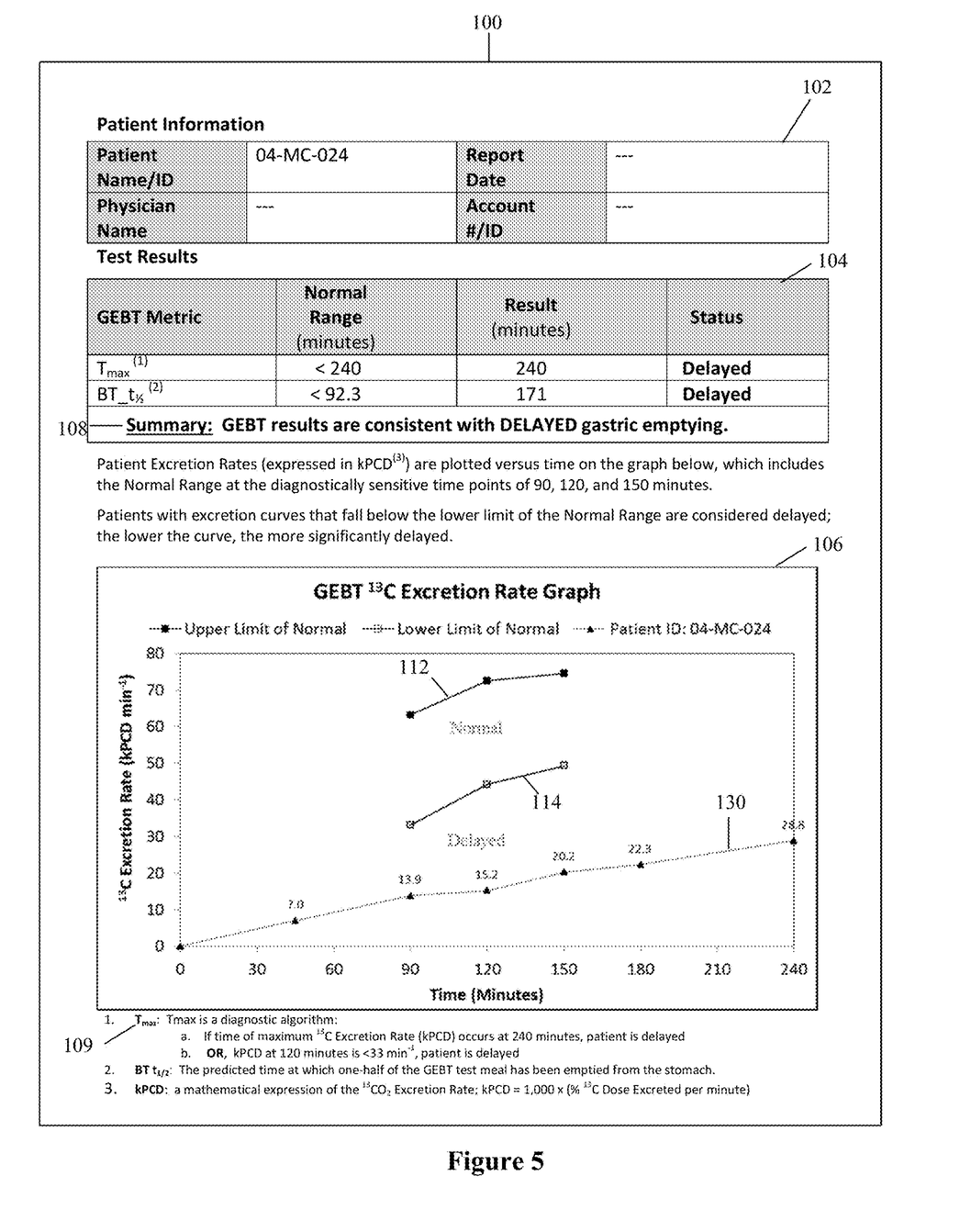
FIG. 5 is a report including a graph of a $^{13}CO_2$ excretion profile for a subject with delayed gastric emptying.

Examples of comprehensive patient profiles which may be provided to clinicians and used by a clinician for patient diagnosis and monitoring based on the results of a gastric emptying breath test are shown in the reports depicted in FIGS. 4 and 5. These reports may be provided in printed form, such as on paper, and/or on a display such as a computer screen. Each report includes a patient information section 102, which in these examples includes spaces designated for displaying the patient name or patient identification number, physician name, account number or account identification number, and report date, which spaces may or may be blank or may include the relevant information. Each report further includes the gastric emptying breath test results 104, which in these examples include the patient's $T_{max}$ and $BT\_T_{1/2}$ measurements, as well as the normal values or ranges for these measurements, and an indication of the patient's status (e.g. normal, delayed) with regard to each measurement. Each report also includes the patients $^{13}CO_2$ excretion graph 106.

In each $^{13}CO_2$ excretion graph 106 of FIGS. 4 and 5, the upper and lower limits of normal reference range are shown by lines 112 and 114 respectively for the 90, 120 and 150 minute time points, which are the most diagnostically sensitive time points when using the kPCD metric. In FIG. 4, line 110 displays the excretion curve of a patient for the duration of the gastric emptying breath test and falls between the upper and lower normal limits 112, 114. In FIG. 5, line 130 displays the excretion curve of a different patient, and the results fall below the lower limit of normal 114.

Each report further includes a summary section 108 indicating whether the gastric emptying breath test results are consistent with normal gastric emptying or delayed gastric emptying, for example. In these examples, the reports further include explanations for the clinician, such as an explanation of the $T_{max}$ diagnostic algorithm 109 that was applied in the report.

Consumption of the entire test meal of a specific caloric value and dose of carbon-13 has been important for breath testing results as the normal reference ranges and cut-off points are established from healthy subjects on this basis. Furthermore, linear regression equations used to estimate $t_{1/2}$ by breath test are derived from the relationship of breath test values to scintigraphic values in patients who have consumed the entire meal. Hence, if a test subject was unable to completely consume the test meal, practitioners of breath tests generally reported inconclusive test results for measurements of gastric emptying and/or suggested that the test subject be re-scheduled for the breath test procedure. However, another particularly useful attribute of using $T_{max}$ for diagnosis is that it is not always necessary for the subject to consume the full meal in order for a diagnosis to be made. For example, even if a test subject could not completely consume the test meal, the patient may be classified as having delayed gastric emptying if $T_{max}$ in such a subject occurs after the $T_{max}$ cut-off value for the test, such as if $T_{max}$ occurs at 240 minutes, or if the subject has a kPCD value that is less than a cut-off value at time t, such as less than 33 at 120 minutes for a four hour breath test. In this way, the patient may be diagnosed as having delayed gastric emptying using $T_{max}$ without needing to be re-scheduled for a repeat test procedure. This is particularly helpful in those patients presenting with significant symptoms of nausea, vomiting, bloating and early satiety.

The applicants performed both statistical analyses and diagnostic precision evaluations on test subjects using the breath test $T_{max}$ metric as compared to diagnosis by scintigraphy. In addition, to demonstrate the exceptional utility and diagnostic performance of $T_{max}$ compared to other breath test metrics, diagnosis by all 3 useful breath test metrics (kPCD, $BT\_t_{1/2}$ and $T_{max}$) were compared to diagnosis by scintigraphy. These analyses and evaluations are discussed in the experimental section below.

EXPERIMENTAL

For these Examples, Applicant analyzed data from a study conducted by Applicant as described in Szarka L, Camilleri M, Vella A, et al. *A Stable Isotope Breath Test with a Standard Meal for Abnormal Gastric Emptying of Solids in the Clinic and in Research. Clin Gastroenterol H.* 2008; 8: 635-643. In the Szarka study, the reported cohort size was 129 subjects who were symptomatic for and suspected of having gastroparesis. However, Applicant excluded 14 subjects due to minor clinical protocol violations, such that the remaining cohort included 115 total subjects. Prior to conducting the Szarka study, the normal reference ranges and the applicable cut-off points for demarcating normal from delayed emptying were established for both breath test (GEBT) and scintigraphy by testing a cohort of 60 healthy subjects with the exact same test meal as that utilized in the Szarka study, a dual labeled test meal that included both $^{13}$C-labeled *Spirulina platensis* with 43 mg $^{13}$C and 0.5 m Ci $^{99m}$Tc sulphur colloid. The normal reference range for each method is the 95% reference interval of the data sets collected from the healthy subjects.

The dual label procedure is a superior method of evaluating agreement between two testing methods. The normal, day-to-day biologic variability of gastric emptying is large and well documented in the literature. For example, when given the same test meal on consecutive days, a test subject will display significant variability in their rate of gastric emptying (on average, the percent coefficient of variation is approximately 12%). Hence, conducting both test methods on the same patient concurrently in the Szarka study and when determining the normal reference ranges eliminated the confounding effects of conducting the breath test on one day and scintigraphy on another day.

Example 1

Applicant analyzed the breath test results of the 60 normal subjects to identify the $T_{max}$ for each subject using a fifth order polynomial curve fitted to the kPCD values at each time point for each subject. The mean time of peak excretion, $T_{max}$, was 161 minutes. Applicant identified a normal $T_{max}$ 95% reference range from the $T_{max}$ values of the 60 normal subjects using Medcalc (version 14.1, 2013). The 95% reference range was 104.6-209.4 minutes.

The excretion profiles (kPCD vs. time) of the 60 normal subjects were averaged and the results are shown in FIG. 1 (the upper curve). The 95% kPCD reference range limits arising from these 60 subjects are lines 12 and 14 of FIGS. 2 and 3.

Example 2

In Example 2, Applicant analyzed the breath test data from the 115 test subjects participating in Applicant's clinical study as described in the Szarka study. As with the 60 normal subjects, Applicant analyzed the breath test results of the test subjects to identify $T_{max}$ for each subject by using a fifth order polynomial curve that was fitted to the kPCD values at each time point. While the 95% $T_{max}$ reference range limit (the "cut-off" point") identified in Example 1 was approximately 209 minutes, Applicants discovered that most of the gastroparetic test subjects (as diagnosed by scintigraphy) had $T_{max}$ values that well exceeded 209 minutes. Most delayed subjects' $T_{max}$ occurred at the end of the evaluation period (at 240 minutes). Applicants further discovered that a small subset of gastroparetic test subjects (as diagnosed by scintigraphy) had a $T_{max}$ that occurred before 209 or 240 minutes, but also had very low excretion profiles (kPCD values vs. time). That is, they were frankly delayed. An example of such a subject is shown in line 40 of FIG. 3. In all cases, such frankly delayed subjects had a kPCD value well below the normal reference range cutoff point at 120 minutes, which is a time point of maximum difference between kPCD values of normal and gastroparetic subjects.

Based on these results, Applicant decided to use the following criteria for diagnosing delayed gastric emptying in the following examples. Curve fitting was omitted and the kPCD value obtained at each time point was used for the evaluation. If maximum excretion rate (kPCD value) occurred at 240 minutes, the patient had delayed gastric emptying. Additionally, if $T_{max}$ occurred prior to 240 minutes, but kPCD at 120 minutes was less than 33 min$^{-1}$, then the subject was likewise classified as having delayed gastric emptying. The value of 33 min$^{-1}$ kPCD was selected as being 25% below the lower reference range limit at 120 minutes.

Example 3

Applicant next used the breath test data and the scintigraphic data obtained from the 115 test subjects to establish a diagnosis for each subject by each test method. Diagnosis (positive or negative for delayed emptying) was established by comparing each test subject's breath test result and, likewise, their scintigraphic test result, to pre-determined cut off points for each test method as described above. The breath test's (GEBT) diagnostic performance vs. scintigraphy was evaluated using kPCD, $BT\_t_{1/2}$ and $T_{max}$ metrics. The applicable cutoff points ("COP's") for the kPCD metric and the breath test $t_{1/2}$ metric ($BT\_t_{1/2}$) are shown in Table 1 below. The COPs for these breath test metrics are the applicable 0.025 fractile bounds (2.5% limit) of the 95% reference interval (normal range) obtained from the 60 healthy subjects. For diagnosis using $T_{max}$, the subject was diagnosed as gastroparetic if $T_{max}$ occurred at 240 minutes, or if $T_{max}$ occurred before 240 minutes but kPCD at 120 minutes was less than 33 min$^{-1}$.

TABLE 1

| | COP's | | | | | | |
|---|---|---|---|---|---|---|---|
| | kPCD COP (min$^{-1}$) Time (min) | | | | | | $BT\_t_{1/2}$ COP |
| | 45 | 90 | 120 | 150 | 180 | 240 | (min) |
| GEBT | 12.9 | 33.1 | 44.2 | 49.3 | 46.5 | 39.2 | 92.3 |
| | Scint_FE COP Time (min) | | | | | | Scint$\_t_{1/2}$ COP |
| | 45 | 90 | 120 | 150 | 180 | 240 | (min) |
| Scintigraphy | 0.181 | 0.494 | 0.678 | 0.774 | 0.875 | 0.957 | 91.0 |

When using the breath test kPCD metric and scintigraphic fraction emptied (FE) metric, test results lower than the COP indicate delayed emptying. Using the 90-minute measurement time as an example, a test subject having a kPCD value<33.1 min$^{-1}$ and a fraction of test meal emptied (FE) by scintigraphy<0.494 would be classified as delayed by both test methods.

Conversely, $t_{1/2}$ represents the time it takes to empty ½ of the test meal from the stomach. When test subjects are delayed, they take longer to empty the stomach. Hence, $t_{1/2}$ values increase as function of increasing gastric delay. By way of example, a test subject having a $BT\_t_{1/2}$ value>92.3 minutes and a scintigraphic $t_{1/2}$ value>91.0 minutes would be classified as delayed by both methods.

Applicant then compared diagnosis obtained by breath test on each subject to diagnosis obtained by scintigraphy on each patient. Breath test diagnoses were established for each patient by each breath test metric (kPCD, BT_$t_{1/2}$ and $T_{max}$). For purposes of this analysis, Applicant considered the scintigraphy results as the true results, or the gold standard. Applicant classified each subject's breath test diagnosis, with reference to the scintigraphic diagnosis, as a true positive (TP), true negative (TN), false positive (FP) or false negative (FN). Using these classifications by each method, Applicant then calculated the breath test's diagnostic performance statistics versus scintigraphy using standard calculations for sensitivity, specificity, concordance, negative predictive value (NPV) and positive predictive value (PPV). Calculations for PPV and NPV incorporated prevalence. The 95% confidence intervals (CI) for the PPV and NPV values were calculated by a statistical bootstrap procedure with 1,000 iterations.

Breath test (GEBT) performance using the three GEBT metrics was compared to three scintigraphic metrics commonly used for diagnosis. The GEBT metrics were: kPCD, BT_$t_{1/2}$, and $T_{max}$. The scintigraphic metrics were: scintigraphic fraction emptied (FE) at corresponding time points, scintigraphic $t_{1/2}$, and scintigraphic fraction of test meal retained at 4 hours.

Table 2 shows a comparison of the results for diagnosis by breath test using kPCD metric vs. diagnosis by scintigraphy using the scintigraphic fraction of test meal emptied metric (Scint_FE). As previously described, when kPCD is used as the sole metric for diagnosis, there is a propensity for the kPCD values of subjects with delayed gastric emptying to rise into the pre-established reference range at later time points. This occurs because at these later time points normal subjects' $^{13}CO_2$ excretion rates are declining while the $^{13}CO_2$ rates of delayed subjects are still rising. Hence, the breath test metric kPCD has an inherent propensity for false negative diagnoses at 180 and 240 minutes when compared to scintigraphic diagnoses. This is reflected in the poor breath test (kPCD) performance characteristics tabulated in Table 2 at 180 and 240 minutes. Thus, diagnostic utility for kPCD metric is best at 90, 120 and 150 minutes.

TABLE 2

Breath Test Performance: kPCD vs. Scint_FE
Diagnosis by kPCD vs. Scint_FE at time t

|  | 45 | 90 | 120 | 150 | 180 | 240 |
|---|---|---|---|---|---|---|
| Classification (N = 115) | | | | | | |
| TP* | 16 | 41 | 48 | 40 | 29 | 15 |
| TN† | 84 | 54 | 45 | 49 | 56 | 62 |
| FP‡ | 6 | 11 | 13 | 13 | 8 | 7 |
| FN§ | 9 | 9 | 9 | 13 | 22 | 31 |
| Performance Statistics (%) | | | | | | |
| Sensitivity | 64.0 | 82.0 | 84.2 | 77.4 | 56.9 | 32.6 |
| Specificity | 93.3 | 83.1 | 77.6 | 79.0 | 87.5 | 89.9 |
| Concordance | 87.0 | 82.6 | 80.9 | 78.3 | 73.9 | 67.0 |
| PPV¶ | 72.7 | 78.8 | 78.7 | 75.9 | 78.4 | 68.2 |
| (95% CI**) | (56.7-89.6) | (69.8-88.7) | (70.5-86.8) | (66.6-84.3) | (66.8-89.6) | (49.2-85.8) |
| NPV†† | 90.3 | 85.7 | 83.3 | 80.3 | 71.8 | 66.7 |
| (95% CI) | (85.6-95.2) | (78.4-92.9) | (74.9-91.7) | (71.2-87.2) | (65.5-79.5) | (61.8-71.6) |

Table 3 below shows a comparison of the results for diagnosis by $T_{max}$ to diagnosis by Scint_FE for each time t. Table 3 (compared to Table 2) shows that $T_{max}$ is much more diagnostically sensitive than diagnosis by kPCD and very useful at later time points. Because $T_{max}$ occurs significantly earlier in normal subjects than in delayed subjects, normal and delayed subjects can be reliably differentiated with this metric. As shown in Table 3, diagnosis by $T_{max}$ has excellent agreement with diagnosis by Scint_FE at each time point.

TABLE 3

Diagnostic Performance of $T_{max}$ vs. Scintigraphy (FE)
Diagnosis by $T_{max}$ vs. Scint_FE at time t,
measured in minutes from the end of test meal consumption

|  | 45 | 90 | 120 | 150 | 180 | 240 |
|---|---|---|---|---|---|---|
| Classification | | | | | | |
| TP | 22 | 44 | 47 | 45 | 43 | 40 |
| TN | 64 | 61 | 57 | 59 | 59 | 61 |
| FP | 26 | 4 | 1 | 3 | 5 | 8 |
| FN | 3 | 6 | 10 | 8 | 8 | 6 |
| Performance Statistics (%) | | | | | | |
| Sensitivity | 88.0 | 88.0 | 82.5 | 84.9 | 84.3 | 87.0 |
| Specificity | 71.1 | 93.8 | 98.3 | 95.2 | 92.2 | 88.4 |

TABLE 3-continued

Diagnostic Performance of $T_{max}$ vs. Scintigraphy (FE)
Diagnosis by $T_{max}$ vs. Scint_FE at time t,
measured in minutes from the end of test meal consumption

|  | 45 | 90 | 120 | 150 | 180 | 240 |
|---|---|---|---|---|---|---|
| Concordance | 74.8 | 91.3 | 90.4 | 90.4 | 88.7 | 87.8 |
| PPV¶ | 45.8 | 91.7 | 97.9 | 93.8 | 89.6 | 83.3 |
| (95% CI) | (37.6-56.0) | (84.1-97.9) | (93.4-100.0) | (87.0-100.0) | (81.5-97.4) | (74.2-92.6) |
| NPV | 95.5 | 91.0 | 85.1 | 88.1 | 88.1 | 91.0 |
| (95% CI) | (90.8-100.0) | (85.7-96.9) | (77.8-92.4) | (81.6-94.6) | (81.4-94.9) | (84.4-96.9) |

Table 4 shows the results for diagnosis by kPCD at 90, 120, and 150 minutes, as well as for diagnosis by $T_{max}$ and $BT\_t_{1/2}$, as compared to diagnosis established by $Scint\_t_{1/2}$. This comparison shows that all three breath test metrics agree well with diagnosis by $Scint\_t_{1/2}$. Diagnosis by $T_{max}$ and/or $BT\_t_{1/2}$ improves diagnostic confidence and is complementary to diagnosis by kPCD at 90, 120, and 150 minutes. Furthermore, it can be seen that $T_{max}$ and $BT\_t_{1/2}$ metrics have similar performance characteristics as compared to scintigraphy, albeit $T_{max}$ is best.

TABLE 4

Breath Test (GEBT) Performance vs. Diagnosis by Scintigraphic t½

|  | Diagnosis by kPCD at 90, 120 and 150 minutes vs. Scint_t$_{1/2}$ | | | Diagnosis by $T_{max}$ and BT_t$_{1/2}$ vs. Scint_t$_{1/2}$ | |
|---|---|---|---|---|---|
|  | 90 Min. | 120 Min. | 150 Min. | $T_{max}$ | $BT\_t_{1/2}$ |
| Classification |  |  |  |  |  |
| TP | 41 | 44 | 40 | 44 | 44 |
| TN | 54 | 48 | 52 | 61 | 55 |
| FP | 11 | 17 | 13 | 4 | 10 |
| FN | 9 | 6 | 10 | 6 | 6 |
| Performance Statistics (%) |  |  |  |  |  |
| Sensitivity | 82.0 | 88.0 | 80.0 | 88.0 | 88.0 |
| Specificity | 83.1 | 73.8 | 80.0 | 93.8 | 84.6 |
| Concordance | 82.6 | 80.0 | 80.0 | 91.3 | 86.1 |
| PPV¶ | 78.8 | 72.1 | 75.5 | 91.7 | 81.5 |
| (95% CI) | (70.5-88.4) | (63.9-81.8) | (66.0-85.7) | (84.7-97.9) | (72.6-90.7) |
| NPV | 85.7 | 88.9 | 83.9 | 91.0 | 90.2 |
| (95% CI) | (78.2-92.9) | (81.2-96.3) | (75.9-91.5) | (84.8-97.2) | (83.1-96.5) |

Example 4

As shown in Table 5, diagnosis by $T_{max}$ using the upper limit of the statistically generated $T_{max}$ 95% Reference Range (104-209 minutes) produces performance statistics akin to simply using 240 minutes as the $T_{max}$ COP for demarcating normal from delayed emptying.

TABLE 5

$T_{max}$ vs. Scintigraphy: $T_{max}$ Curve Fit COP (209 minutes) vs. 240 Minute COP

|  | $T_{max}$ > 209 min (no caveat) vs. Scint_t$_{1/2}$ > 91.0 min | $T_{max}$ > 209 min kPCD$_{120}$ < 33 vs. Scint_t$_{1/2}$ > 91.0 min | Gastroparetic if $T_{240}$ = maximum or kPCD$_{120}$ < 33 vs. Scint_t$_{1/2}$ > 91.0 min |
|---|---|---|---|
| Classification |  |  |  |
| N = 115 |  |  |  |
| TP* | 43 | 46 | 44 |
| TN† | 59 | 58 | 61 |
| FP‡ | 6 | 7 | 4 |
| FN§ | 7 | 4 | 6 |
| Performance |  |  |  |
| Sensitivity | 86.0 | 92.0 | 88.0 |
| Specificity | 90.8 | 90.8 | 93.8 |
| Concordance | 88.7 | 91.3 | 91.3 |
| PPV¶ | 87.8 | 88.5 | 91.7 |
| NPV** | 89.4 | 93.7 | 91.0 |

Diagnosis by breath test was compared to diagnosis by Scint_FE at 240 minutes. Relevant scintigraphic literature indicates that 4 hours (240 minutes) may be the best single measurement time for diagnosis of gastroparesis. This is because patients symptomatic for gastroparesis are not always frankly delayed or frankly normal throughout a gastric emptying evaluation. However, with regards to evaluating patients symptomatic for gastroparesis, later time points may be generally more sensitive in detecting delayed emptying than earlier time points. Therefore, breath test diagnostic performance, when utilizing $kPCD_{(t)}$, $BT\_t_{1/2}$ and $T_{max}$ metrics, was compared to Scint_FE diagnosis obtained at 240 minutes. The results are shown in Table 6 below.

TABLE 6

Breath Test (GEBT) Performance vs. Scintigraphic Classification at 4 Hours

Diagnosis by GEBT: $kPCD_{(t)}$, $T_{max}$ and $BT\_t_{1/2}$
vs. Diagnosis by Scint_FE at 240 minutes

|  | kPCD at 90 min | kPCD at 120 min | kPCD at 150 min | $T_{max}$ | $BT\_t_{1/2}$ |
|---|---|---|---|---|---|
| Classification (N = 115) | | | | | |
| TP | 36 | 38 | 36 | 40 | 37 |
| TN | 53 | 46 | 52 | 61 | 52 |
| FP | 16 | 23 | 17 | 8 | 17 |
| FN | 10 | 8 | 10 | 6 | 9 |
| Performance Statistics (%) | | | | | |
| Sensitivity | 78.3 | 82.6 | 78.3 | 87.0 | 80.4 |
| Specificity | 76.8 | 66.7 | 75.4 | 88.4 | 75.4 |
| Concordance | 77.4 | 73.0 | 76.5 | 87.8 | 77.4 |
| PPV¶ | 69.2 | 62.3 | 67.9 | 83.3 | 68.5 |
| (95% CI**) | (59.9-79.5) | (54.6-71.3) | (58.0-78.0) | (74.5-92.4) | (59.5-79.0) |
| NPV | 84.1 | 85.2 | 83.9 | 91.0 | 85.2 |
| 95% CI) | (76.9-91.9) | (77.2-93.4) | (75.9-91.8) | (84.8-97.0) | (77.6-93.5) |

As shown in Table 6 above, diagnosis by $T_{max}$ shows excellent agreement with diagnosis by Scint_FE at 240 minutes and is superior to either diagnosis by kPCD or $BT\_t_{1/2}$.

Example 5

The positive predictive value (PPV) and negative predictive value (NPV) of the breath test (GEBT) are important indicators of how confident one can be that the breath test result (diagnosis), in the absence of a comparative scintigraphic test result, is correct. A high PPV value means that when the breath test yields a positive result (for example "delayed"), it is most likely correct in its assessment. Likewise, a high NPV value means that a negative diagnosis by breath test is most likely correct in its assessment compared to scintigraphy. The PPV and NPV values associated with diagnosis by each breath test metric vs. scintigraphy are reported in prior Tables 2-5. As can be seen, the PPV and NPV values associated with diagnosis by $T_{max}$ are superb, very good by $BT\_t_{1/2}$ and good by kPCD. However, PPV and NPV values for a disorder are influenced by the prevalence of the disorder in the population being tested. Breath testing may be utilized in a referred patient population that is symptomatic for accelerated or delayed emptying (gastroparesis). Hence, the need to assess breath test PPV and NPV values across varying prevalence fractions in the intended use population is important and of particular interest to regulatory authorities if the test is intended for commercial use.

Based on an extensive scintigraphic literature review, the prevalence of gastroparesis in referral centers that conduct gastric emptying evaluations may range from 27% to 57%. To see what effect changing the prevalence would have on the diagnostic performance of $T_{max}$, the PPV and NPV values were calculated using a prevalence of 27% and of 57%. The PPV and NPV values and their two-sided 95% confidence intervals were calculated using a statistical bootstrap procedure in which the set of 115 test subjects was sampled 1000 times with replacement to best estimate the PPV and NPV values. Standard equations that incorporate prevalence were used to compute the PPV and NPV values.

The results are shown in Tables 7 and 8 below. A mean PPV or NPV value of 1.0 represents 100% confidence that the breath test result would be consistent with a true scintigraphic test result.

The PPV and NPV values associated with diagnosis by $T_{max}$ were compared to diagnosis by scintigraphic fraction emptied (Scint_FE) at each measurement time throughout the 4-hour evaluation period and shown in Table 7. The upper and lower limits of the 95% Confidence Intervals around the mean values of the PPV and NPV values are co-reported. Calculations were performed at 3 levels of prevalence: 27%; the actual prevalence of gastroparesis found at each measurement time in the cohort of 115 test subjects (Szarka study); and 57%. The prevalence at each time point for the cohort of 115 test subjects was established with reference to the pre-established Scint_FE cut-off point at each measurement time. As noted, a statistical bootstrap procedure using 1000 samplings of the data from the 115 test subjects with replacement was used to obtain the best estimate of the true PPV and NPV values.

TABLE 6

Bootstrap-Derived $T_{max}$ PPV and NPV Values Across Changing Prevalence of Gastroparesis (Diagnosis by $T_{max}$ vs. Scint_(FE)

| | | | Time Points (minutes) | | | | | |
|---|---|---|---|---|---|---|---|---|
| Prevalence (%) | Statistic | 95% CI | 45 | 90 | 120 | 150 | 180 | 240 |
| 27 | PPV | Mean PPV | 0.5332 | 0.8459 | 0.9481 | 0.8703 | 0.8017 | 0.7414 |
| | | SD | 0.0454 | 0.0676 | 0.0495 | 0.0652 | 0.0719 | 0.0675 |
| | | Upper | 0.6261 | 0.9582 | 1.0000 | 1.0000 | 0.9490 | 0.8828 |
| | | Lower | 0.4490 | 0.7148 | 0.8336 | 0.7400 | 0.6610 | 0.6162 |
| | NPV | Mean NPV | 0.9423 | 0.9556 | 0.9383 | 0.9443 | 0.9406 | 0.9474 |
| | | SD | 0.0303 | 0.0160 | 0.0177 | 0.0167 | 0.0181 | 0.0189 |
| | | Upper | 1.0000 | 0.9848 | 0.9691 | 0.9761 | 0.9749 | 0.9811 |
| | | Lower | 0.8749 | 0.9226 | 0.9013 | 0.9112 | 0.9044 | 0.9095 |
| Study Prevalence 45 min = 21.7 90 min = 43.4 120 min = 49.6 150 min = 46.0 180 min = 44.4 240 min = 40.0 | PPV | Mean PPV | 0.4595 | 0.9197 | 0.9798 | 0.9391 | 0.8979 | 0.8317 |
| | | SD | 0.0469 | 0.0369 | 0.0205 | 0.0324 | 0.0397 | 0.0469 |
| | | Upper | 0.5604 | 0.9794 | 1.0000 | 1.0000 | 0.9740 | 0.9255 |
| | | Lower | 0.3762 | 0.8405 | 0.9336 | 0.8701 | 0.8153 | 0.7416 |
| | NPV | Mean NPV | 0.9554 | 0.9126 | 0.8514 | 0.8808 | 0.8827 | 0.9103 |
| | | SD | 0.0235 | 0.0299 | 0.0362 | 0.0341 | 0.0350 | 0.0313 |
| | | Upper | 1.0000 | 0.9686 | 0.9242 | 0.9462 | 0.9487 | 0.9693 |
| | | Lower | 0.9081 | 0.8568 | 0.7778 | 0.8163 | 0.8137 | 0.8441 |
| 57 | PPV | Mean PPV | 0.8023 | 0.9503 | 0.9844 | 0.9589 | 0.9338 | 0.9096 |
| | | SD | 0.0287 | 0.0242 | 0.0154 | 0.0225 | 0.0276 | 0.0283 |
| | | Upper | 0.8572 | 0.9880 | 1.0000 | 1.0000 | 0.9852 | 0.9643 |
| | | Lower | 0.7450 | 0.8998 | 0.9472 | 0.9107 | 0.8748 | 0.8519 |
| | NPV | Mean NPV | 0.8255 | 0.8589 | 0.8112 | 0.8272 | 0.8173 | 0.8363 |
| | | SD | 0.0813 | 0.0462 | 0.0469 | 0.0457 | 0.0486 | 0.0524 |
| | | Upper | 1.0000 | 0.9477 | 0.8975 | 0.9194 | 0.9155 | 0.9355 |
| | | Lower | 0.6611 | 0.7689 | 0.7181 | 0.7412 | 0.7253 | 0.7372 |

Other than the 45 minute time point, the PPV and NPV values associated with diagnosis by $T_{max}$ were superb and consistent at each time point and across changing prevalence. The 45 minute time point was not useful for diagnosis of gastroparesis when using either breath test or scintigraphy as this is the time point at which the least number of positive subjects were identified by either test method throughout the evaluation period.

To further explore confidence in the $T_{max}$ metric, PPV and NPV values across changing prevalence fractions were calculated when diagnosis by $T_{max}$ was compared to diagnosis by scintigraphic $t_{1/2}$ across changing prevalence fractions. $BT\_t_{1/2}$ was co-explored in the same analysis.

The PPV and NPV values associated with diagnosis by $T_{max}$ and $BT\_t_{1/2}$ were compared to diagnosis by scintigraphic $t_{1/2}$. Calculations were performed at 3 levels of prevalence: 27%; 43.5%; and 57%. The prevalence number of 43.5% is the prevalence of gastroparesis found in the 115 subjects where classification (normal or delayed) was established relative to the scintigraphic $t_{1/2}$ cut-off point of 91.0 minutes. As noted, a statistical bootstrap procedure using 1000 samplings from the 115 test subjects data set with replacement was used to best estimate the true PPV and NPV values.

TABLE 8

Bootstrap-Derived $BT\_t_{1/2}$ and $T_{max}$ PPV and NPV Values Across Changing Prevalence of Gastroparesis (Diagnosis by $BT\_t_{1/2}$ and $T_{max}$ vs. Scint_$t_{1/2}$).

| Prevalence (%) | Statistic | 95% CI | $BT\_t_{1/2}$ | $T_{max}$ |
|---|---|---|---|---|
| 27 | PPV | Mean PPV | 0.6846 | 0.8442 |
| | | SD | 0.0669 | 0.0673 |
| | | Upper | 0.8187 | 1.0000 |
| | | Lower | 0.5616 | 0.7148 |
| | NPV | Mean NPV | 0.9503 | 0.9547 |
| | | SD | 0.0180 | 0.0173 |
| | | Upper | 0.9830 | 0.9844 |
| | | Lower | 0.9124 | 0.9165 |
| Study Prevalence 43.5 | PPV | Mean PPV | 0.8152 | 0.9178 |
| | | SD | 0.0455 | 0.0368 |
| | | Upper | 0.9074 | 0.9793 |
| | | Lower | 0.7258 | 0.8468 |
| | NPV | Mean NPV | 0.9023 | 0.9134 |
| | | SD | 0.0349 | 0.0317 |
| | | Upper | 0.9649 | 0.9719 |
| | | Lower | 0.8307 | 0.8478 |
| 57 | PPV | Mean PPV | 0.8842 | 0.9497 |
| | | SD | 0.0313 | 0.0240 |
| | | Upper | 0.9418 | 1.0000 |
| | | Lower | 0.8212 | 0.8998 |
| | NPV | Mean NPV | 0.8443 | 0.8566 |
| | | SD | 0.0506 | 0.0492 |
| | | Upper | 0.9416 | 0.9461 |
| | | Lower | 0.7440 | 0.7537 |

Once again, PPV and NPV values associated with $T_{max}$ were superb across changing prevalence. $BT\_t_{1/2}$ also exhibited very good PPV and NPV values, but they were not as good as $T_{max}$.

The examples show that $T_{max}$ may be used for diagnosing gastroparesis with a very high level of confidence when prevalence is low or high in the intended use population. $T_{max}$ is therefore a unique and useful tool for diagnosing delayed gastric emptying.

What is claimed is:

1. A breath test method for identifying delayed gastric emptying based on solid phase gastric emptying, comprising:

supplying a test subject with a solid breath test meal having a $^{13}$C-*Spirulina platensis* label, wherein the solid breath test meal has a caloric content of between about 200 kCal and about 400 kCal;

selecting a plurality of time points at which to collect breath samples from the test subject, the plurality of time points including a first time point and a last time point after the test subject consumes the solid breath test meal, wherein the last time point is four hours after the test subject consumes the solid breath test meal;

collecting breath samples of the test subject at the plurality of time points;

providing an instrument configured to measure a ratio of $^{13}CO_2/^{12}CO_2$ in the breath samples;

measuring the ratio of $^{13}CO_2/^{12}CO_2$ in the breath samples using the instrument;

generating $^{13}CO_2$ excretion measurements from the breath samples;

comparing the $^{13}CO_2$ excretion measurements of the breath samples;

determining that the $^{13}CO_2$ excretion measurement of the breath sample collected at four hours is higher than the $^{13}CO_2$ excretion measurements of all the other breath samples collected;

determining that the $^{13}CO_2$ excretion measurement for each successive breath sample is higher than a $^{13}CO_2$ excretion measurement of the respective breath sample collected immediately prior thereto, wherein $^{13}CO_2$ excretion for the test subject reaches a maximum after the last time point;

determining that the test subject has delayed gastric emptying; and administering a treatment to the test subject after determining that the test subject has delayed gastric emptying, wherein the treatment comprises administering an effective amount of prokinetic agents, antiemetic agents, antihistamine agents or erythromycin lactobionate to the test subject.

2. The breath test method of claim 1 wherein said solid breath test meal has a $^{13}$C label in a dose of between about 20 mg to about 80 mg.

3. The breath test method of claim 1 wherein the prokinetic agents comprise dopamine D2-receptor antagonists, metoclopramide, or domperidone.

4. The breath test method of claim 1 wherein the antiemetic agents comprise phenothiazines, prochlorperazine, or thiethylperazine.

5. The breath test method of claim 1 wherein the antihistamine agents include promethazine.

6. The breath test method of claim 1 wherein the instrument is a mass spectrometer or an infrared spectrometer.

7. The breath test method of claim 1 wherein the $^{13}CO_2$ excretion measurements are measured in units of kPCD so as to normalize for height, weight, age, and gender of the test subject.

8. The breath test method of claim 1 wherein the time points include 45 minutes, 90 minutes, 120 minutes, 150 minutes, 180 minutes, and 240 minutes after the test subject consumes the solid breath test meal.

\* \* \* \* \*

UNITED STATES PATENT AND TRADEMARK OFFICE
CERTIFICATE OF CORRECTION

PATENT NO. : 11,134,883 B2
APPLICATION NO. : 13/926715
DATED : October 5, 2021
INVENTOR(S) : Williams et al.

Page 1 of 1

It is certified that error appears in the above-identified patent and that said Letters Patent is hereby corrected as shown below:

On the Title Page

Item (51), under "Int. Cl.", Lines 2-5, delete
"*A61M 36/14*   (2006.01)
*A61B 5/00*    (2006.01)
*A61B 5/08*    (2006.01)
*A61K 49/00*   (2006.01)" and insert -- *A61M 36/14*   (2006.01) --, therefor.

Column 2, item (56), under "OTHER PUBLICATIONS", Line 8, delete "Westminister," and insert -- Westminster, --, therefor.

In the Specification

In Column 8, Line 18, delete "130." and insert -- $^{13}$C. --, therefor.

In Column 10, Line 64, delete "erythomycin" and insert -- erythromycin --, therefor.

In Column 12, Line 3, delete "(e.g." and insert -- (e.g., --, therefor.

In Column 12, Line 66, delete "Clin Gastroenterol" and insert -- Clin. Gastroenterol. --, therefor.

Signed and Sealed this
Eighth Day of March, 2022

Drew Hirshfeld
*Performing the Functions and Duties of the
Under Secretary of Commerce for Intellectual Property and
Director of the United States Patent and Trademark Office*